(12) United States Patent
Zhang et al.

(10) Patent No.: US 9,447,199 B2
(45) Date of Patent: *Sep. 20, 2016

(54) METHOD FOR EXTRACTING BROWN ALGAE POLYSACCHARIDE VIA MICROWAVE CHEMICAL PROCESS

(71) Applicant: Shenyang Kesi High-Technology Co, Ltd., Shenyang, Liaoning Province (CN)

(72) Inventors: Jinsong Zhang, Shenyang (CN); Mingtian Li, Shenyang (CN); Zhiyu Liu, Shenyang (CN); Lei Xu, Shenyang (CN)

(73) Assignee: SHENYANG KESI HIGH-TECHNOLOGY CO. LTD., Shenyang, Liaoning Province (CN)

( * ) Notice: Subject to any disclaimer, the term of this patent is extended or adjusted under 35 U.S.C. 154(b) by 7 days.

This patent is subject to a terminal disclaimer.

(21) Appl. No.: 14/355,535

(22) PCT Filed: Nov. 1, 2012

(86) PCT No.: PCT/CN2012/083932
§ 371 (c)(1),
(2) Date: Apr. 30, 2014

(87) PCT Pub. No.: WO2013/067896
PCT Pub. Date: May 16, 2013

(65) Prior Publication Data
US 2014/0296496 A1    Oct. 2, 2014

(30) Foreign Application Priority Data

Nov. 7, 2011 (CN) .......................... 2011 1 0348242

(51) Int. Cl.
*C08B 37/00* (2006.01)
*C08L 5/04* (2006.01)
(52) U.S. Cl.
CPC ....... *C08B 37/0084* (2013.01); *C08B 37/0003* (2013.01); *C08L 5/04* (2013.01)

(58) Field of Classification Search
CPC .. C08B 37/0003; C08B 37/0084; C08L 5/04
USPC ............................... 514/3; 536/123.1, 3, 124
See application file for complete search history.

(56) References Cited

FOREIGN PATENT DOCUMENTS

| CN | 101250232 | 8/2008 |
| CN | 101993501 | 3/2011 |
| CN | 102180990 | 9/2011 |
| CN | 102417549 | 4/2012 |
| JP | 63316731 | 12/1988 |

OTHER PUBLICATIONS

International Search Report issued in PCT Application No. PCT/CN2012/083932.

*Primary Examiner* — Shaojia Anna Jiang
*Assistant Examiner* — Michael C Henry
(74) *Attorney, Agent, or Firm* — Lucas & Mercanti, LLP

(57) ABSTRACT

This invention relates to an extraction process of brown algae polysaccharides in a field of pharmaceutical chemistry. This invention particularly discloses a process of extracting brown algae polysaccharides based on a microwave chemistry method and brown algae polysaccharides obtained by said process. The process of the invention comprises: 1) putting pulverized brown algae powder into a microwave reaction chamber, adding acid solution to conduct reaction; optionally concentrating the mixer, and then washing with organic solvent to remove excess acid; conducting grading alcohol precipitation after water extract to obtain mannuronic acid rich fragment (M rich) algin, fucoidan and/or laminaran respectively; and adding an alkali solution to the brown algae residue to conduct alkaline digestion, filtering the residue off, adjusting pH of the filtrate to neutral, conducting alcohol precipitation to obtain guluronic acid rich fragment (G rich) algin precipitates. The present invention has significant advantages like fast processing rate, high yield of polysaccharides, strong controllable polysaccharide degradation, using less organic acid and efficient recovery, small water consumption, low power consumption, etc., the active polysaccharides has high yield and content, better water-soluble, and good biological activities.

27 Claims, 1 Drawing Sheet

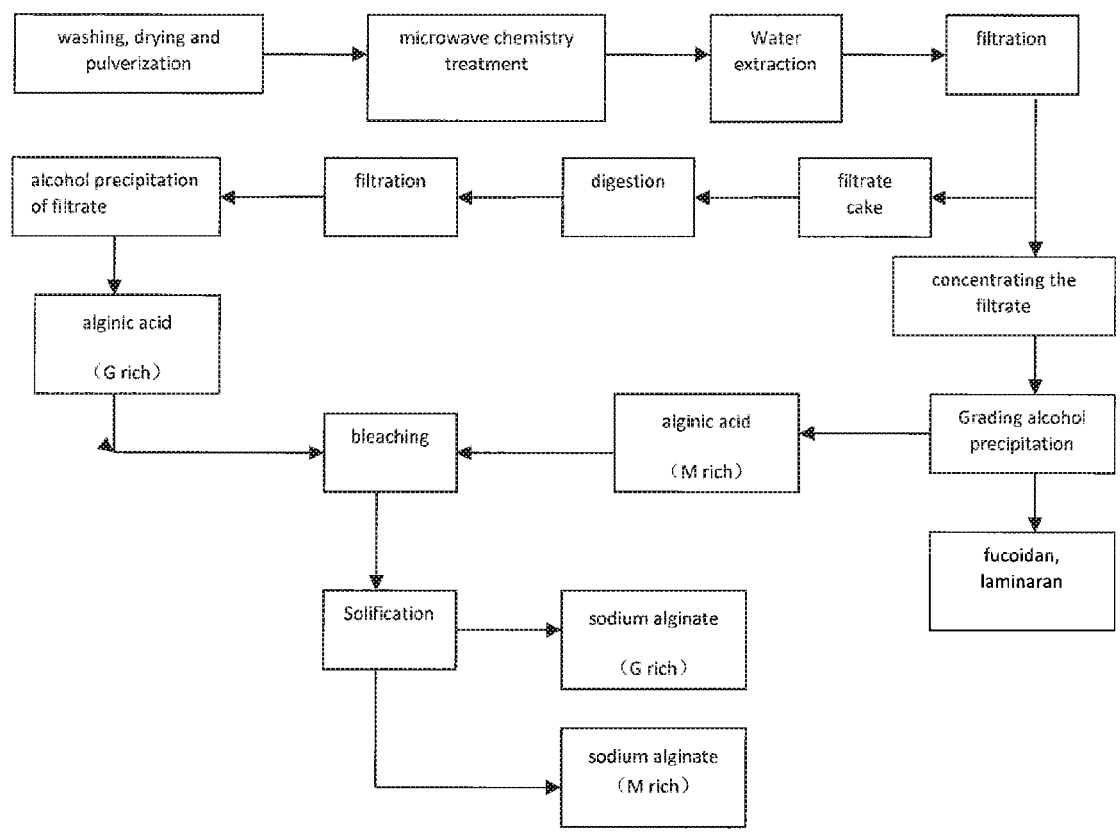

METHOD FOR EXTRACTING BROWN ALGAE POLYSACCHARIDE VIA MICROWAVE CHEMICAL PROCESS

CROSS-REFERENCE TO RELATED APPLICATIONS

This application is a U.S. national stage of PCT/CN2012/083932 filed on Nov. 1, 2012 which claims the benefit of priority from Chinese Patent Application No. 201110348242.6 filed Nov. 7, 2011, the contents of each of which are incorporated herein by reference.

TECHNICAL FIELD

This invention relates to the pharmaceutical chemistry field, relates to an extraction process of brown algae polysaccharides, and particularly is a process of extracting brown algae polysaccharides based on a microwave chemistry method.

DESCRIPTION OF BACKGROUND

Algae, a collective term of marine algae, usually attaching to a seabed or some solid structures, is a single or a series of simple plant comprising of basic cells. Nutrients in algae include polysaccharides, proteins, lipids, pigments and low molecular weight substances. Proven by traditional Chinese medicine and modern scientific research, the main component of substances having activity of enhancing immunity and anti-cancer activity in algae is polysaccharides.

Algae includes red algae, green algae, brown algae, etc., and current research and application of algae polysaccharides mainly focus on brown algae polysaccharides. Brown algae is a higher class of algae, having about 250 genera and more than 1500 species. The body of brown algae is in yellow brown or dark brown and contains substances like polysaccharides, proteins, lipids, mannitol, etc. Some members of the class, such as *japonica*, also contain a lot of iodine in their cells.

Brown algae polysaccharides are important components of brown algae, including algin, fucoidan, laminaran, etc. Algin, usually referring to sodium alginate, is a linear copolymer with polysaccharide homopolymeric blocks of (1-4)-linked β-D-mannuronate (M) and α-L-guluronate (G) residues, which has a high content in brown algae. There are three types of segment chain structure thereof: M blocks of continuous M units, G blocks of continuous G units, and a MG block formed with alternately connected G and M units. Algin is also the most representative class of algae chemical products. Data shows that algin annual production in China is the highest in the world. For ease of storage and use, algin is generally converted into sodium alginate as a final product. As a sodium salt of poly anionic polysaccharide (alginic acid), sodium alginate has a very wide range of applications in industry for its inherent physical and chemical properties.

In food industry, sodium alginate is an excellent food additive, for its low calorie, nontoxicity, easy expansion, and high flexibility, and for when it is added to foods it plays many functions like coagulation, thickening, emulsifying, suspending, stabilizing, food drying prevention, etc.

In textile industry, sodium alginate has features like easy to color, high color yield, color bright and softening printed fabrics, etc., and is most commonly used paste in cotton fabrics reactive dye printing. Meanwhile, it can also be used as soluble fiber in industrial processes such as warp slurry, water proof processing, and lace manufacture.

In cosmetic industry, sodium alginate is used as toothpaste base, shampoos, hair setting agent, etc. In paper industry, it is used as sizing. In rubber industry, it can be used as latex concentrate, and also can be made as water-based coatings and water-resistant coating.

Sodium alginate is also an important biomedical material, being widely used as drug delivery agent, polymer film, cell encapsulation, wound dressings, surgical sponge, embolic agent, etc. It is attracting more and more attention in biomedical material science, clinical medicine, tissue engineering and pharmaceutical science and other fields. So far, algin production basically still uses alkaline digestion, the basic principle of which is to use sodium carbonate ($Na_2CO_3$) to convert various water-insoluble alginate salts into sodium alginate, to dissolve sodium alginate in water, and to obtain dry sodium alginate powder through filtration, acid/calcium precipitation, and sodium salt conversion.

Fucoidan is a heteropolysaccharide, comprising fucose and sulfate, as well as monosaccharides including galactose, xylose, mannose, uronic acid, etc. Due to its unique structure and excellent physiological activity, such as regulating blood lipids, lowing blood sugar, lowing blood pressure, anti-clotting, anti-tumor, anti-mutagenic and anti-radiation, anti-virus, enhancing immune function, etc., fucoidan has become one of hotspots of marine drug research of this century. Laminaran, is also a polysaccharide with a variety of physiological activities. The preparation of fucoidan and laminaran mainly utilizes wastes from the production of algin, iodine, and mannitol as main raw materials, which are subjected to grading-alcohol precipitation after water soaking.

Current algin production process has the following major disadvantages:

It has heavy water and energy consumption, and heavy pollution. This is also one of the key factors restricting the development of the algae industry. Alkaline digestion is simple in principle, but often requires dozens of processes in actual industrial production, some of which are very difficult. For example, in the concentrated sodium alginate slurry formed from *japonica* through the treatment of sodium carbonate, many water-insoluble cellulose and other ingredients need to be filtered. Due to high viscosity of the concentrated slurry, in addition to the addition of a filtering aid like diatomite, it also need consume a large amount of water for dilution, and has high requirements in quality of the water used. According to statistics, the production of one ton of finished sodium alginate needs about 700-1000 tons of water. Further, there are mainly two approaches i.e. acid addition and calcium salt addition in the chemical process of conventional alkaline digestion: first, water-insoluble alginate salts in brown algae are converted into water-soluble sodium alginate, adding acid or calcium ions makes sodium alginate form alginic acid or calcium alginate precipitates which after washing is converted back to sodium alginate, and finally sodium alginate is further processed into various products. Whichever method is used, it will produce a large amount of industrial waste water, which poses a serious threat to the ecological environment.

Meanwhile, current sodium alginate product is a single product variety, lack excellent quality, and have low added value. Sodium alginates in term of structure can be divided into three categories: high G/M ratio, medium G/M ratio, and low G/M ratio, in term of viscosity can be divided into ultra-low viscosity, low viscosity, medium viscosity, high viscosity, and ultra-high viscosity sodium alginate, in term of purity can be divided into three levels: industrial, food and medical. The current domestic production of sodium alginate are mostly medium-viscosity products. As health or pharmaceutical products, its application is limited due to its strong gelling property, low solubility, etc., and its activity cannot be fully achieved.

To overcome these difficulties, domestic and oversea researchers made long-term efforts on those processes targeting above disadvantages, and achieved a lot of important progress and accomplishments. These studies include improvement of the conventional process and development of a new process. For instance, a recently reported new process of algin reactive extrusion by foreign scholars has advantages like water-saving, time-saving, less alkaline use, etc., and the viscosity and the yield of the product get some degree of improvements, but the process cannot directly produce water-soluble polysaccharide with good biological activities. Modification to conventional algae polysaccharide products includes using biological, chemical or physical methods to degrade sodium alginate and fucoidan to alginate oligosaccharides, oligosaccharides, and low molecular weight fucose, to adjust sulfur content of fucoidan, etc.

Researches also confirmed that the activities of sodium alginate and fucoidan after degradation has been effectively improved, some low molecular weight sodium alginates already show heparin-like anti-tumor and anti-viral physiological activities and can be used for cardiovascular disease and virus medicinal research. Some of them have intestine adjustment and detoxification, lowering blood glucose and lipid, anti-clotting, anti-inflammatory, immunomodulatory effects and can be used as dietary food for diabetes, obesity, colorectal cancer, and habitual constipation patients.

Especially in recent years, unique physiological functions of modified low molecular weight algin or fucoidan continues to be discovered, and its activity and medicinal value has become one of the new research hotspots.

Further, polymannuronic acid (M) and polyguluronic acid (G) are unique components in algin molecule, and have not been found independently exist in nature. When the proportion of the two alduronic acid polysaccharides (M/G), or the structure and arrangement of such a block in algin varies, the performance of the algin will exhibit significantly difference. Therefore, there are many researchers obtain different polysaccharide fragments and oligosaccharide thereof with unique structures through different degradation and separation methods, as to study the unique biological activity thereof, and to develop drugs with special efficacy.

All these series of oligosaccharides or oligose with different structures greatly enrich the diversity of algae polysaccharide products. However, these studies all use algin of medium viscosity as raw materials, and does not fundamentally solve the problems in conventional production process of sodium alginates, like heavy water and energy consumption, heavy pollution, low yield/content, etc.

Microwave assisted rapid method for hydrolysis of sodium alginate for M/G ratio determination (Mahesh Chhatbar, *Carbohydrate Polymers* Vol 76 (2009) 650-656) discloses in a home-use microwave oven, using a oxalic acid solution or a dilute sulfuric acid solution as solvent partially degrades sodium alginate, and its main purpose is to find a simple, rapid, and mild method to determine the M/G (mannuronic acid/guluronic acid) ratio in sodium alginate. However, the sodium alginate material used in this method is still prepared by conventional extraction methods, and does not overcome heavy water and energy consumption and other defects in the conventional process.

Microwave assisted desulfation of sulfated polysaccharides (Diego A, Navaroo, *Carbohydrate Polymers* Vol 69 (2007) 742-747) discloses in a home use microwave oven, using a microwave-assisted method removes sulfur from red algae polysaccharide *carrageenan*, agar and fucoidan in brown algae, animal polysaccharides chondroitin sulfate, as to overcome the shortcomings of commonly used hydrochloric acid desulfurization method. The method still uses polysaccharides as starting material and has not overcome the defects like heavy water and energy consumption, etc. In addition, the purpose of pursuit of high desulfurization rate in the paper is intended to improve convenience of analyzing samples, and does not take into account the activity of polysaccharides.

Therefore, it is necessary to continue to carry out the research and development of new technology, new technology, new product in marine science and seaweed industry.

SUMMARY OF THE INVENTION

To overcome above technical defects, the present invention provides a novel process of extracting brown algae polysaccharides, i.e. a process of extracting brown algae active polysaccharides via a microwave chemistry method. The process of extracting brown algae active polysaccharides via a microwave chemistry method of the invention comprises the following steps of:

1) putting pulverized brown algae powder into a microwave reaction chamber, adding acid solution of a mass concentration of 5% to 99%, conducting reaction of the mixer for 5-120 mins at a microwave power of mass power density of 1 kilowatt per kilogram of material-10 kilowatts per kilogram of material under a work pressure of 20 mmHg-760 mmHg; optionally concentrating the mixer, and then washing with organic solvent to remove excess acid.

2) adding water solution into the product obtained from step 1) for water extraction, concentrating the extracting solution, adjusting pH to neutral with a base, conducting grading alcohol precipitation to obtain mannuronic acid rich fragment (M rich) algin, fucoidan and/or laminaran respectively; and remaining brown algae residue.

3) adding an alkali solution to the brown algae residue of step 2), conducting alkaline digestion reaction at a temperature of 35-60° C. for 20-80 mins, filtering the residue off, adjusting pH of the filtrate to neutral, conducting alcohol precipitation after concentration to obtain guluronic acid rich fragment (G rich) algin precipitates.

In the process of the present invention, the pulverized brown algae powder is brown algae powder obtained using conventional methods of pulverization in the field, or commercially available pulverized brown algae powder is purchased and directly used in the process of the invention, wherein the mesh size of the pulverized brown algae powder is regular one in the field, or is determined by one skilled person in the art in the combination of the present invention and common knowledge.

In the process of the present invention, as one of the embodiments, where in the acid solution added in step 1), an organic acid is a non-volatile acid, there is no need to remove the acid by concentration after the microwave reaction; where an organic acid added is volatile acid, after the microwave reaction is completed, concentration is conducted to remove the acid, preferably by microwave heating under reduced pressure, and then washing with organic solvent is conducted to remove a small amount of residual acid.

In the process of the present invention, as one of the embodiments, the application method of the microwave power in said step 1) is a continuous microwave mode or a combination of continuous microwave and pulse microwave modes; wherein in the embodiment of using the combination of continuous microwave and pulse microwave, the continuous microwave irradiation is first used until the reflux of the acid solution, then the irradiation is converted to pulse microwave for 5 min-120 min; continuous microwave is also kept for 5 min-120 min after the reflux of the solution.

In the process of the present invention, as one of further preferred embodiments, in said step 1), in the case of continuous microwave, mass power density is 1 kilowatt per kilogram of material-5 kilowatts per kilogram of material; in the case of pulse microwave, mass power density is 2 kilowatts per kilogram of material-10 kilowatts per kilogram of material, the duty ratio is A/B, where A=1 sec-100 sec, B=1 sec-100 sec.

In the process of the present invention, the selection of the microwave reaction chamber can be determined by one skilled person in the art in combination of the present invention and common knowledge in the art, which is either a traveling wave microwave reaction chamber or a resonant microwave reaction chamber.

In the process of the present invention, as one of the embodiments, in said step 1), range of weight ratio of the brown algae raw material and the acid solution=5/1-1/5.

In the process of the present invention, as one of the embodiments, the acid solution in step 1) is selected from an organic acid or a mixed solution of an organic acid and an inorganic acid.

In the process of the present invention, as one of further embodiments, the organic acid is selected from oxalic acid of a weight concentration of 5% to 50%, preferably oxalic acid of 10%-35%; formic acid of 10%-99%, preferably formic acid of 30-85%; acetic acid of 10%-99%, preferably acetic acid of 60-95%; or propionic acid of 10%-99%, preferably propionic acid aqueous solution of 70-95%.

The acid solutions of above mentioned concentration can be directly commercially purchased, or be prepared using conventional methods in the field, for instance, adding an appropriate amount of water into an acid of a concentration of 100% (e.g., pure formic acid) to dilute said acid to the corresponding concentration.

In the process of the present invention, as one of the embodiments, when a mixed solution of organic and inorganic acids is used, in a mixed solution of organic acid and inorganic acid, the concentration of the organic acid in the mixed solution is above defined concentration of the organic acid; and mass percentage concentration of the inorganic acid is 0.1%-15%; as one of further preferred embodiments, the inorganic acid is selected from hydrochloric acid, sulfuric acid, nitric acid or phosphoric acid.

Above mentioned inorganic acid solution can be commercially available, and then using conventional methods prepares the corresponding concentration of the organic-inorganic mixed acid solution, for instance adding hydrochloric acid of a concentration of 36% to the organic acid to reach the corresponding concentration.

In the process of the present invention, controllable degradation of brown algae polysaccharides can be achieved by controlling the reaction conditions, utilizing cooperative effects among microwave, organic acid molecules and brown algae polysaccharides, and selectively cleaving the glycosidic bonds of brown algae polysaccharides.

In the process of the present invention, as one of the embodiments, in said step 1), the organic solvent used to wash the residue acid is selected from methanol, ethanol, propanol or acetone, or a combination of two or more thereof. There is no special requirement on the concentration of the organic solvent, which can be determined by one skilled person in the art with the combination of prior art or common knowledge in the field.

In the process of the present invention, as one of the embodiments, in the step 2), the amount of water is 5-8 times of the volume of the obtained product in step 1). One skilled person in the art with the combination of the present invention and common knowledge can adjust the amount by adding or reducing; when the extracting solution is concentrated, the extracting solution is preferably concentrated to 1/5-1/8 of the original volume thereof.

In the process of the present invention, as one of the embodiments, in step 2), the base used for pH adjustment is selected from sodium carbonate or sodium hydroxide; wherein sodium carbonate or sodium hydroxide are sodium carbonate or sodium hydroxide solutions in a concentration commonly used in the art; its main purpose is to complete the conversion of alginic acid to sodium alginates.

In the process of the present invention, as one of the embodiments, the grading alcohol precipitation in said step 2) comprises: adding ethanol to 20 wt %-40 wt % alcohol content, conducting centrifugation or filtration to obtain a mannuronic acid-rich fragment oligo algin precipitates; then adding ethanol to 60 wt %-70 wt % alcohol content, conducting filtration or centrifugation to obtain fucoidan precipitates; and finally adding ethanol to 80 wt %-85 wt % alcohol content, conducting filtration or centrifugation to obtain laminaran precipitates.

In the process of the present invention, as one of the embodiments, the base of said step 3) is selected from sodium carbonate or sodium hydroxide; wherein sodium carbonate or sodium hydroxide are sodium carbonate or sodium hydroxide solutions in a concentration commonly used in the art.

In the process of the present invention, as one of the embodiments, the acid used to adjust pH value in the step 3) is selected from hydrochloric acid, wherein the hydrochloric acid is a hydrochloric acid solution in a concentration commonly used in the art.

In the process of the present invention, as one of the embodiments, wherein alcohol used in the alcohol precipitation in said step 3) is selected from ethanol or methanol. When ethanol or methanol is used in alcohol precipitation, in principle the alcohol is added to the solution until there is no precipitation, and preferably until the alcohol content in the solution reaches 80%-85%.

In the process of the present invention, brown algae used to extract brown algae polysaccharides using the process of the present invention include but are not limited to, *Laminaria* (*Laminaria*) *japonica, Sargassum* (*Sargassum*) *sargassum*, sea millet, *fusiforme, Sargassum*, creeping Sargasso sticks, *Fucus* (*Fucus*) *fucus*, bladderwrack, *Pelvetia* (*Pelvetia*) *carrageenan, Undaria* (*Undaria*) *wakame* or *Maerocystis* (*Maerocystis*) *kelp*.

As one of the preferred embodiments, the present invention also provides a process of preparing active polysaccharides using *Laminaria japonica*. The process is as follows: putting dry *japonica* powder into a microwave extract chamber, adding 60%-85% formic acid of 0.5 to 1.5 times of its weight, at a microwave power density 1-2 KW/Kg under 500 mmHg-760 mmHg pressure maintaining the reflux of formic acid solution for 15-30 min, and then evaporating under reduced pressure the formic acid solution to dryness. An ethanol solution of 3-5 times of the weight of the *japonica* powder is added to the reaction chamber. The mixer is stirred and washed for 40-60 minutes and filtered. The filter residue after drying is extracted twice with water, wherein each time the amount of water is 4-6 times of the weight of the residue, the extraction temperature is 60-80° C., and the extraction time is about 40 minutes. Filtration is conducted and the two filtrate solutions are combined, neutralized with a sodium hydroxide solution until neutral, and concentrated to a volume of 1/5 of the extract; then ethanol is added to the solution until 35% ethanol content, and the solution stands for 4-8 hours and is filtered; and the filtrate cake is washed with anhydrous ethanol and ether and is dried to obtain polysaccharide A; ethanol continues to be added to the filtrate until 65% ethanol content of the solution, and the solution stands for 4-8 hours and is filtered; and the filtrate cake is washed with anhydrous ethanol and ether and is dried to obtain polysaccharide B. Ethanol continues to be added to the filtrate until 85% ethanol content of the solution, and the solution stands for 4-8 hours and is filtered; and the filtrate cake is washed with anhydrous ethanol and ether and is dried to obtain polysaccharide C.

The *japonica* residue after above aqueous extraction is added with a sodium carbonate solution, at a temperature of 35-60° C. for alkaline digestion reaction for about 40 minutes, filtered, and the filtrate is adjusted to neutral pH with hydrochloric acid, concentrated and is subjected to alcohol precipitation to obtain polysaccharide D.

Wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

As one of the preferred embodiments, the present invention also provides a process of preparing active polysaccharides using *Sargassum fusiforme*. The process is as follows: putting dry *fusiforme* powder into a microwave extract chamber, adding 10%-20% oxalic acid solution of 0.5 to 1.5 times thereof, at a microwave power density 1-2 KW/Kg under 500 mmHg-760 mmHg pressure maintaining the reflux of oxalic acid solution for 15-25 min, and then evaporating under reduced pressure the solution to dryness. An ethanol solution of 4-6 times of the weight of the *fusiforme* powder is added to the reaction chamber. The mixer is stirred and washed for 40-60 minutes and filtered, and the filter residue is dried. The filtrate is distilled to recycle ethanol and oxalic acid. The filter residue after drying is extracted twice with water, wherein each time the amount of water is 4-6 times of the weight of the residue, the extraction temperature is 70° C., and the extraction time is about 40 minutes; the above two filtrate solutions after filtration are combined, neutralized with a sodium hydroxide solution until neutral, and concentrated to a volume of 1/5 of the extract; then ethanol is added to the solution until 30% ethanol content, and the solution stands for 4-8 hours and is filtered; and the filtrate cake is washed with anhydrous ethanol and ether and is dried to obtain polysaccharide A; ethanol continues to be added to the filtrate until 60% ethanol content of the solution, and the solution stands for 4-8 hours and is filtered; and the filtrate cake is washed with anhydrous ethanol and ether and is dried to obtain polysaccharide B. Ethanol continues to be added to the filtrate until 80% ethanol content of the solution, and the solution stands for 4-8 hours and is filtered; and the filtrate cake is washed with anhydrous ethanol and ether and is dried to obtain polysaccharide C. The *fusiforme* residue after above aqueous extraction is added with a sodium carbonate solution, at a temperature of 35-60° C. for alkaline digestion reaction for 40-60 minutes, filtered, and the filtrate is adjusted to neutral pH with hydrochloric acid, concentrated and is subjected to alcohol precipitation to obtain polysaccharide D.

Wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

As one of the preferred embodiments, the present invention also provides a process of preparing active polysaccharides using *Fucus fucus*. The process is as follows: putting dry *fucus* powder into a microwave extract chamber, adding 80%-95% propionic acid solution of 1 to 2 times thereof, at a microwave power density 3-5 KW/Kg, after propionic acid solution refluxes, maintaining for 40-60 minutes under 500 mmHg-760 mmHg pressure, and then evaporating under reduced pressure the propionic acid solution to dryness. An ethanol solution of 3-5 times of the weight of the *fucus* powder is added to the reaction chamber. The mixer is stirred and washed for 30-60 minutes and filtered, and the filter residue is dried. The filter residue after drying is extracted with water of 4-6 times of the weight of the residue, is extracted at 70° C. for 40 minutes, and is filtered; the above extraction process is repeated again. The two filtrate solutions after filtration are combined, neutralized with a sodium hydroxide solution until neutral, and concentrated to a volume of 1/5 of the extraction solution; then ethanol is added to the solution until 35% ethanol content, and the solution stands for 4-8 hours and is filtered; and the filtrate cake is washed with anhydrous ethanol and ether and is dried to obtain polysaccharide A; ethanol continues to be added to the filtrate until 65% ethanol content of the solution, and the solution stands for 4-8 hours and is filtered; and the filtrate cake is washed with anhydrous ethanol and ether and is dried to obtain polysaccharide B. Ethanol continues to be added to the filtrate until 85% ethanol content of the solution, and the solution stands for 4-8 hours and is filtered; and the filtrate cake is washed with anhydrous ethanol and ether and is dried to obtain polysaccharide C. The *fucus* residue after above aqueous extraction is added with a sodium carbonate solution, at a temperature of 35-60° C. for alkaline digestion reaction for 40-60 minutes, filtered, and the filtrate is adjusted to neutral pH with hydrochloric acid, concentrated and is subjected to alcohol precipitation to obtain polysaccharide D.

Wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

As one of the preferred embodiments, the present invention also provides a process of preparing active polysaccharides using *Pelvetia carrageenan*. The process is as follows: putting dry *carrageenan* powder into a microwave extract chamber, adding an oxalic acid-hydrochloric acid mixed solution of 0.5-2 times thereof, wherein the content of oxalic acid in the mixed solution is 20% and the content of hydrochloric acid is 0.1%, at a microwave power density 1-2 KW/Kg under 500 mmHg-760 mmHg pressure maintaining the reflux of mixed acid solution for 15-25 minutes, and then evaporating under reduced pressure the solution to dryness. An ethanol solution of 3-5 times of the weight of the *carrageenan* powder is added to the reaction chamber. The mixer is stirred for 30-60 minutes and filtered. The filter residue after drying is extracted with water of 4-6 times of the weight of the residue, is extracted at 70° C. for 40 minutes, and is filtered; the above extraction process is repeated again. The two filtrate solutions after filtration are combined, neutralized with a sodium hydroxide solution until neutral, and concentrated to a volume of 1/5 of the extract; then ethanol is added to the solution until 35% ethanol content, and the solution stands for 4-8 hours and is filtered; and the filtrate cake is washed with anhydrous ethanol and ether and is dried to obtain polysaccharide A;

ethanol continues to be added to the filtrate until 65% ethanol content of the solution, and the solution stands for 4-8 hours and is filtered; and the filtrate cake is washed with anhydrous ethanol and ether and is dried to obtain polysaccharide B. Ethanol continues to be added to the filtrate until 85% ethanol content of the solution, and the solution stands for 4-8 hours and is filtered; and the filtrate cake is washed with anhydrous ethanol and ether and is dried to obtain polysaccharide C. The *carrageenan* residue after above water extraction is added with a sodium carbonate solution, at a temperature of 35-60° C. for alkaline digestion reaction for 40-60 minutes, filtered, and the filtrate is adjusted to neutral pH with hydrochloric acid, concentrated and is subjected to alcohol precipitation to obtain polysaccharide D.

Wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

As one of the preferred embodiments, the present invention also provides a process of preparing active polysaccharides using *Undaria wakame*. The process is as follows: putting dry *wakame* powder into a microwave extract chamber, adding formic acid-hydrochloric acid mixed solution of 0.5 to 2.5 times thereof, wherein the content of formic acid is 80% and the content of hydrochloric acid is 0.5% at a microwave power density 2-4 KW/Kg under 500 mmHg-760 mmHg pressure maintaining the reflux of mixed acid solution for 10-30 min, and then evaporating under reduced pressure the mixed acid solution to dryness. An ethanol solution of 3-5 times of the weight of the *wakame* powder is added to the reaction chamber. The mixer is stirred and washed for 30-60 minutes and filtered. The filter residue after drying is extracted with water of 4-6 times of the weight of the residue, is extracted at 60° C. for 40 minutes, and is filtered; the above extraction process is repeated again. The two filtrate solutions after filtration are combined, neutralized with a sodium hydroxide solution until neutral, and concentrated to a volume of 1/5 of the extract; then ethanol is added to the solution until 35% ethanol content, and the solution stands for 4-8 hours and is filtered; and the filtrate cake is washed with anhydrous ethanol and ether and is dried to obtain polysaccharide A; ethanol continues to be added to the filtrate until 65% ethanol content of the solution, and the solution stands for 4-8 hours and is filtered; and the filtrate cake is washed with anhydrous ethanol and ether and is dried to obtain polysaccharide B. Ethanol continues to be added to the filtrate until 85% ethanol content of the solution, and the solution stands for 4-8 hours and is filtered; and the filtrate cake is washed with anhydrous ethanol and ether and is dried to obtain polysaccharide C. The *wakame* residue after above water extraction is added with a sodium carbonate solution, at a temperature of 35-60° C. for alkaline digestion reaction for 40-60 minutes, filtered, and the filtrate is adjusted to neutral pH with hydrochloric acid, concentrated and is subjected to alcohol precipitation to obtain polysaccharide D.

Wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

As one of the preferred embodiments, the present invention also provides a process of preparing active polysaccharides using *Maerocystis kelp*. The process is as follows: putting dry *kelp* powder into a microwave extract chamber, adding 80%-95% acetic acid solution of 0.3 to 1.2 times thereof, at a microwave power density 1-4 KW/Kg under 500 mmHg-760 mmHg pressure maintaining the reflux of acetic acid solution for 30-40 minutes, and then evaporating under reduced pressure the acetic acid solution to dryness. An ethanol solution of 3-5 times of the weight of the *kelp* powder is added to the reaction chamber. The mixer is stirred and washed for 30-60 minutes and filtered. The filter residue after drying is extracted with water of 4-6 times of the weight of the residue, is extracted at 60° C. for 40 minutes, and is filtered; the above extraction process is repeated again. The two filtrate solutions after filtration are combined, neutralized with a sodium hydroxide solution until neutral, and concentrated to a volume of 1/5 of the extract; then ethanol is added to the solution until 35% ethanol content, and the solution stands for 4-8 hours and is filtered; and the filtrate cake is washed with anhydrous ethanol and ether and is dried to obtain polysaccharide A; ethanol continues to be added to the filtrate until 65% ethanol content of the solution, and the solution stands for 4-8 hours and is filtered; and the filtrate cake is washed with anhydrous ethanol and ether and is dried to obtain polysaccharide B. Ethanol continues to be added to the filtrate until 85% ethanol content of the solution, and the solution stands for 4-8 hours and is filtered; and the filtrate cake is washed with anhydrous ethanol and ether and is dried to obtain polysaccharide C. The *kelp* residue after above water extraction is added with a sodium carbonate solution, at a temperature of 35-60° C. for alkaline digestion reaction for 40-60 minutes, filtered, and the filtrate is adjusted to neutral pH with hydrochloric acid, concentrated and is subjected to alcohol precipitation to obtain polysaccharide D.

Wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

The present invention also provides a brown algae polysaccharides prepared using the process of the invention, wherein said brown algae polysaccharides is obtained using the process of the invention.

As one of the preferred embodiments, the present invention also provides a guluronic acid-rich fragment (G rich) algin or a mannuronic acid-rich fragment (M rich) algin prepared using the process of the invention;

As one of the preferred embodiments, the guluronic acid-rich fragment (G rich) align is preferably guluronic acid-rich fragment (G rich) *japonica* algin, *fusiforme* algin, focus algin, carrageen algin, *wakame* algin, or *kelp* algin;

As one of the preferred embodiments, the mannuronic acid-rich fragment (M rich) align is preferably mannuronic acid-rich fragment (M rich) *japonica* algin, *fusiforme* algin, focus algin, carrageen algin, *wakame* algin, or *kelp* algin.

The present invention also provides a process of preparing mannuronic acid-rich fragment (M rich) sodium alginate, wherein said process is: the mannuronic acid-rich fragment (M rich) algin prepared using the process of the invention is added with sodium carbonate to be converted to mannuronic acid-rich fragment (M rich) sodium alginate.

The present invention also provides a mannuronic acid-rich fragment (M rich) sodium alginate prepared using the process of the invention.

The present invention has the following features:

Firstly, using a microwave with an organic acid directly works on brown algae raw materials, utilizing the organic acid cleaves various bonds between polysaccharides and organic macromolecules (including cellulose and algin) of cell walls of brown algae raw materials, as to promote the release of polysaccharides from said medicinal materials and improve the extraction rate of polysaccharides; besides regarding the organic acid, in addition to H$^+$ ions's degradation effects on polysaccharides, organic acid radical ions can protect polysaccharide molecules by forming hydrogen bonds with hydroxyl groups of the polysaccharides.

Secondly, the organic acid enhanced by microwave can further moderately degrade released polysaccharides, thereby significantly enhancing the water-solubility of the polysaccharides. Polysaccharides with relatively centralized molecular weight distribution and good water-solubility are obtained and the whole process achieves the efficient extraction and restructuring of brown algae polysaccharides.

Thirdly, brown algae polysaccharides with different molecular structures have various sensitivity to the microwave radiation and the organic acids. The molecular weight of M-rich fragments which are relatively sensitive to the degradation effect of organic acids under microwave radiation in brown algae significantly decreases, water solubility thereof significantly increases, and it can be successfully extracted without hydrolysis.

G rich fragments which are not sensitive to the degradation effects of organic acid under microwave radiation remain in the brown algae residue, and can be extracted via the alkaline digestion process, and thereby the separation process of M rich align and G rich algin is simplified.

Fourthly, microwave heating can ensure inside and outside of the materials are simultaneously heated and sufficiently overcome a series of insurmountable issues like uneven heating of materials and high energy consumption in conventional heating methods.

Compared with prior art, the present invention further has the following advantages:

1. The present invention saves time, uses less acids and has easy and efficient recycling and remarkable water and energy saving effects. Using microwave heating technology effectively overcomes the heat problem which is difficult to avoid in conventional heating methods, significantly reducing the amount of organic acids used and processing time, especially in the distillation process of removing acids, can overcome the uneven heating problem which is insurmountable in conventional heating methods. This feature in the large-scale production has been particularly remarkable.

2. The organic acids enhanced by microwave can further moderately adjust the molecular structure of released brown algae polysaccharides, including moderately degrading algin, improving its water solubility, and achieving the separation of M-rich fragments and G-rich fragments. The sulfur content of brown algae polysaccharides containing sulfur can be moderately reduced. The present process uses acids which directly work on medicinal raw materials, overcomes many deficiencies of polysaccharide extraction in the existing processes. Currently, researches on various modifications on brown algae polysaccharides basically use brown algae polysaccharides as raw materials, and cannot overcome many problems in the polysaccharide extraction.

3. The polysaccharide products obtained by the present invention has narrow molecular weight distribution, high purity, good water solubility, and good activity. The process of the present invention has distinct advantages in large-scale industrial production.

BRIEF DESCRIPTION OF THE DRAWINGS

FIG. 1 is a process flow diagram of the present invention.

EMBODIMENTS

The present invention will be further described by the following Examples and Experimental Examples, but the present invention is not limited thereto.

The process of the present invention is as follows:

1) putting brown algae raw materials after washing, drying and pulverization into a microwave reactor chamber, adding an organic acid or an organic/inorganic acid mixed solution thereinto, sufficiently stirring to make the powder be well wetted;

2) microwave treatment, applying microwave power, using cooperative effects among microwave, organic acid molecules and brown algae polysaccharides, selectively cutting the glycosidic bonds of the brown algae polysaccharides, as to achieve controllable degradation thereof;

3) using distillation under reduced pressure by microwave heating to remove most of the organic acids or the organic/inorganic acid mixed solution, and sufficiently washing with an organic solvent to remove a small amount of residual acid to complete the microwave pretreatment of brown algae;

4) adding about 5-8 times of water to extract microwave pretreated brown algae, wherein the extracting solution after concentration is subjected to grading alcohol precipitation to obtain excellent water-soluble mannuronic acid rich fragment (M rich) algin, fucoidan and laminaran;

5) microwave pretreated brown algae raw material residue after the water extraction is subjected to alkaline digestion process, to obtain guluronic acid rich fragment (G rich) algin.

The whole process is shown in FIG. 1.

In order to evaluate the novel process, there are control processes designed according to references in each of the embodiments, and comparing data of corresponding extraction yields of sodium alginate, fucoidan, and laminaran, total water consumption in the process, viscosity of sodium alginate products, reaction time, amount of organic acids (or mixed acid) used, and sulfate content of fucoidan from the control process, the novel process, the conventional heating method in each of the examples are listed. Sodium alginate products are purified by an appropriate method to obtain monomer polysaccharides with an uniform composition, wherein polymannuronic acid fragment (M) and guluronic acid fragment (G) thereof are measured by a H$^1$-NMR method to obtain the ratio M/G (see book "sugar complex biochemical research"), the molecular weight of sodium alginate is determined by using high performance liquid chromatography (Wenjing Tai, Guangli Yu, Jiandong Wu, Xia Zhao, Extract and physicochemical properties of four types of algae polysaccharides, Journal of Ocean University of China, 2010, 40(5):23-26), the sulfate content of fucoidan is measured by nephelometry (Jianbo Cong, Changzhen Wang, Yan Li, etc., Measurement of sulfate group content of brown algae sulfated polysaccharides—study of barium sulfate nephelometry [J] Pharmaceutical Journal of Chinese People's Liberation Army, 2003, 19 (3):181).

Comparative Example 1

Control process: 100 g *japonica* powder raw material after being washed, dried, pulverized is weighted and placed in a 2 L beaker, and 1 L water and 20 g sodium carbonate are added into the beaker. The mixer is stirred in a water bath of 70° C. for 1 hour, and then is diluted with 80-100 L water, followed by sufficient stirring and filtration. The filtrate is adjusted to pH 2.0 by adding hydrochloric acid and is centrifuged. The precipitate is converted to sodium alginate by adding sodium carbonate. The resulting supernatant is subjected to grading ethanol precipitation to obtain fucoidan (by adding ethanol up to the alcohol content of 65 wt %) and laminaran (by adding ethanol up to the alcohol content of 85 wt %). Products obtained via each of the steps are dried to calculate extraction yields thereof, wherein the extraction yield is the weight percentage of the product of each step and raw material *japonica* powder. All analytical results are shown in Table 1.

Example 1

1) 1.5 kg dry *japonica* powder is placed in a traveling wave microwave reaction chamber;

2) 0.5 L anhydrous acid and 0.25 L water are mixed to prepare 0.75 L 70% formic acid solution;

3) 0.75 L formic acid in step 2) is added into the microwave reaction chamber in step 1), and the mixer is sufficiently stirred to evenly wet the *japonica* powder;

4) the wetted material in step 3) is subjected to irradiation at 5 KW continuous microwave power until the liquid refluxes, i.e., the organic acid solution is vaporized, and then the microwave is switched to a pulsed microwave power operating mode, wherein the duty ratio is 5 seconds/5 seconds (i.e. the ratio of on-time and off-time), peak power is 10 KW; after 12 min, vacuuming is conducted (reaction chamber working pressure is 20 mmHg) for reduced pressure distillation until there is no liquid in the microwave reaction chamber; microwave pretreatment of *japonica* powder is completed;

5) 5 L absolute ethanol is added into 1.5 kg the pretreated *japonica* powder, sufficiently stirred, and filtered, wherein the filtrate is distilled to recover ethanol, and the residue after being dried is microwave pretreated *japonica* powder;

6) 100 g microwave pretreated *japonica* powder in step 5) is placed in a 1 L beaker, 500 ml distill water is added thereinto, and the mixer is placed in a hot water bath at 70° C. for 40 min for extraction and then filtered. The above procedure is repeated once. The two filtrates are combined and pH thereof is adjusted to neutral, and residue is maintained for further process;

7) The filtrate in step 6) is concentrated and is subjected to grading ethanol precipitation to obtain M rich fragment sodium alginate (by adding ethanol to the alcohol content of 30 wt %), fucoidan (by adding ethanol to the alcohol content of 65 wt %) and laminaran (by adding ethanol to the alcohol content of 85 wt %);

8) 500 ml water and 6 g sodium carbonate are added into the residue in step 6), the mixer is stirred in a hot water bath at 70° C. for 40 min, and filtered. The filtrate is neutralized and concentrated, and is subjected to alcohol precipitation to give G rich fragment sodium alginate.

Data including extraction yields of products in each step, total water consumption in the process, viscosity of sodium alginate products, sulfate content of fucoidan, etc. are listed in Table 1.

TABLE 1

Comparison results of polysaccharide extraction yield of each step, total amount of water consumption, viscosity of sodium alginate and sulfate content of fucoidan between using microwave pretreated *japonica* dry powder and using untreated *japonica* dry powder raw materials:

| | Control Process | Novel Process |
|---|---|---|
| Water consumption (water/*japonica* powder) | 100/1 | 15/1 |
| Yield of sodium alginate (wt) | 16.2% | 10.1% (M Rich) 6.2% (G Rich) |
| Yield of algin (wt) | 1.4% | 4.0% |
| Yield of laminaran (wt) | 1.0% | 1.0% |

TABLE 1-continued

Comparison results of polysaccharide extraction yield of each step, total amount of water consumption, viscosity of sodium alginate and sulfate content of fucoidan between using microwave pretreated *japonica* dry powder and using untreated *japonica* dry powder raw materials:

| | Control Process | Novel Process |
|---|---|---|
| Molecular weight of sodium alginate | $1.5 \times 10^6$ | $1.2 \times 10^5$ (M Rich) |
| Sulfate content of fucoidan (wt) | 15.5% | 6.9% |
| Amount of base (base/*japonica* powder) | 0.2 | 0.05 |
| Amount of organic acid solution (liquid/solid) | — | 1/2 |
| Sodium alginate M/G | 2.22 | 8.52 (M Rich) |
| Processing time (min) | 60 | 12 |

Comparative Example 2

Control process: 100 g *fusiforme* powder raw material after being washed, dried, pulverized is weighted and placed in a 2 L beaker, and 1 L water and 25 g sodium carbonate are added into the beaker. The mixer is stirred in a water bath of 70° C. for 1 hour, and then is diluted with 80-100 L water, followed by sufficient stirring and filtration. The filtrate is adjusted to pH 2.0 by adding hydrochloric acid and is centrifuged. The precipitate is converted to sodium alginate by adding sodium carbonate. The resulting supernatant is subjected to grading ethanol precipitation to obtain fucoidan (by adding ethanol up to the alcohol content of 65 wt %) and laminaran (by adding ethanol up to the alcohol content of 85 wt %). Parameters regarding the products are measured according to Comparative Example 1. All analysis results are shown in Table 2.

Example 2

1) 1.5 kg dry *fusiforme* powder is placed in a traveling wave microwave reaction chamber;

2) 180 g oxalic acid and 1.5 L water are mixed to prepare a 10% oxalic acid solution;

3) 1.5 L oxalic acid solution in step 2) is added into the microwave reaction chamber in step 1), and the mixer is sufficiently stirred to evenly wet the *fusiforme* powder;

4) the wetted material in step 3) is subjected to irradiation at 3 KW continuous microwave power until liquid refluxes, i.e., the organic acid solution is vaporized, and then the microwave is switched to a pulsed microwave power operating mode, wherein the duty ratio is 5 seconds/5 seconds, peak power is 5 KW; after 15 min, vacuuming is conducted (reaction chamber working pressure is 100 mmHg) for reduced pressure distillation to remove the organic acid solution until there is no liquid in the microwave reaction chamber; microwave pretreatment of *fusiforme* powder is completed;

5) 5 L absolute ethanol is added into 1.5 kg pretreated *fusiforme* powder in step 4), sufficiently stirred, and filtered, wherein the filtrate is distilled to recover ethanol and oxalic acid, and the residue after being dried is microwave pretreated *fusiforme* powder;

6) 100 g microwave pretreated *fusiforme* powder in step 5) is placed in a 1 L beaker, 500 ml distill water is added thereinto, and the mixer is placed in a hot water bath at 70° C. for 40 min for extraction and then filtered. The above procedure is repeated once. The two filtrates are combined and pH thereof is adjusted to neutral, and residue is maintained for further process;

7), 8) steps are the same as ones in Example 1.

Data including extraction yields of products in each step, total water consumption in the process, viscosity of sodium alginate products, sulfate content of fucoidan, etc. are listed in Table 2.

TABLE 2

Comparison results of polysaccharide extraction yield of each step, the total amount of water consumption, the viscosity of sodium alginate and the sulfate content of fucoidan between using microwave pretreated *fusiforme* dry powder and using untreated *fusiforme* dry powder raw materials:

|  | Comparative process | Novel Process |
|---|---|---|
| Water consumption (water/*fusiforme* powder) | 100/1 | 15/1 |
| Yield of sodium alginate (wt) | 24.4% | 10.5% (M Rich) 14.5% (G Rich) |
| Yield of algin (wt) | 1.4% | 3.2% |
| Yield of laminaran (wt) | 0.8% | 0.8% |
| Molecular weight of sodium alginate | $2.1 \times 10^6$ | $3.7 \times 10^4$ (M Rich) |
| Sulfate content of fucoidan (wt) | 16.8% | 8.3% |
| Amount of base (base/*fusiforme* powder) | 0.25 | 0.05 |
| Amount of organic acid solution (liquid/solid) |  | 1/1 |
| Sodium alginate M/G | 0.66 | 5.43 (M Rich) |
| Processing time (min) | 60 | 15 |

Comparative Example 3

Control process: 100 g *kelp* powder raw material after being washed, dried, pulverized is weighted and placed in a 2 L beaker, and 1 L water and 25 g sodium carbonate are added into the beaker. The mixer is stirred in a water bath of 70° C. for 1 hour, and then is diluted with 80-100 L water, followed by sufficient stirring and filtration. The filtrate is adjusted to pH 2.0 by adding hydrochloric acid and is centrifuged. The precipitate is converted to sodium alginate by adding sodium carbonate. The resulting supernatant is subjected to grading ethanol precipitation to obtain fucoidan (by adding ethanol up to the alcohol content of 65 wt %) and laminaran (by adding ethanol up to the alcohol content of 85 wt %). Parameters regarding the products are measured according to Comparative Example 1. All analysis results are shown in Table 3.

Example 3

1) 1.5 kg dry *kelp* powder is placed in a resonant wave microwave reaction chamber;

2) 0.4 L acetic anhydride and 0.1 L water are mixed to prepare 0.5 L 80% acetic acid solution;

3) 0.5 L acetic acid solution in step 2) is added into the microwave reaction chamber in step 1), and the mixer is sufficiently stirred to evenly wet the *kelp* powder;

4) the wetted material in step 3) is subjected to irradiation at 2 KW continuous microwave power until liquid refluxes, i.e., the organic acid solution is vaporized, and then the microwave is switched to a pulsed microwave power operating mode, wherein the duty ratio is 5 seconds/5 seconds, peak power is 4 KW; after 35 mins, vacuuming is conducted (reaction chamber working pressure is 200 mmHg) for reduced pressure distillation to remove the organic acid solution until there is no liquid in the microwave reaction chamber;

5) 5 L absolute ethanol is added into the microwave reaction chamber in step 4), sufficiently stirred, and filtered, wherein the filtrate is distilled to recover ethanol, and the residue after being dried is microwave pretreated *kelp* powder;

6) 100 g microwave pretreated *kelp* powder in step 5) is placed in a 1 L beaker, 500 ml distill water is added thereinto, and the mixer is placed in a hot water bath at 70° C. for 40 mins for extraction and then filtered. The above procedure is repeated once. The two filtrates are combined and pH thereof is adjusted to neutral, and residue is maintained for further process;

7), 8) steps are the same as ones in Example 1.

Data including extraction yields of products in each step, total water consumption in the process, viscosity of sodium alginate products, sulfate content of fucoidan, etc. are listed in Table 3.

TABLE 3

Comparison results of polysaccharide extraction yield of each step, the total amount of water consumption, the viscosity of sodium alginate and the sulfate content of fucoidan between using microwave pretreated kelp dry powder and using untreated kelp dry powder raw materials:

|  | Comparative process | Novel Process |
|---|---|---|
| Water consumption (water/kelp powder) | 100/1 | 15/1 |
| Yield of sodium alginate (wt) | 24.6% | 16.0% (M Rich) 8.8% (G Rich) |
| Yield of algin (wt) | 0.6% | 3.5% |
| Yield of laminaran (wt) | 0.6% | 0.6% |
| Molecular weight of sodium alginate | $1.15 \times 10^6$ | $7.8 \times 10^4$ (M Rich) |
| Sulfate content of fucoidan (wt) | 15.5% | 6.8% |
| Amount of base (base/kelp powder) | 0.25 | 0.05 |
| Amount of organic acid solution (liquid/solid) | — | 1/3 |
| Sodium alginate M/G | 1.56 | 7.55 (M Rich) |
| Processing time (min) | 60 | 35 |

Comparative Example 4

Control process: 100 g *wakame* powder raw material after being washed, dried, pulverized is weighted and placed in a 2 L beaker, and 1 L water and 25 g sodium carbonate are added into the beaker. The mixer is stirred in a water bath of 70° C. for 1 hour, and then is diluted with 80-100 L water, followed by sufficient stirring and filtration. The filtrate is adjusted to pH 2.0 by adding hydrochloric acid and is centrifuged. The precipitate is converted to sodium alginate by adding sodium carbonate. The resulting supernatant is subjected to grading ethanol precipitation to obtain fucoidan (by adding ethanol up to the alcohol content of 65 wt %) and laminaran (by adding ethanol up to the alcohol content of 85 wt %). Parameters regarding the products are measured according to Comparative Example 1. All analysis results are shown in Table 4.

Example 4

The differences from Example 1 are:
1) 1.5 kg dry *wakame* powder after being dried, decontaminated and pulverized is placed in a resonant wave microwave reaction chamber;
2) 0.8 L anhydrous formic acid, 0.15 L water and 0.05 L 20% hydrochloric acid solution are mixed to prepare 1 L formic acid-hydrochloric acid mixed solution, wherein the content of formic acid is 83% and the content of hydrochloric acid is 0.1%;
3) 1 L acid mixed solution in step 2) is added into the microwave reaction chamber in step 1), and the mixer is sufficiently stirred to evenly wet the *wakame* powder;
4) the wetted material in step 3) is subjected to irradiation at 3.5 KW continuous microwave power until liquid refluxes, i.e., the organic acid solution is vaporized, and then the microwave is switched to a pulsed microwave power operating mode, wherein the duty ratio is 5 seconds/5 seconds, peak power is 7 KW; after 13 mins, vacuuming is conducted (reaction chamber working pressure is 150 mmHg) for reduced pressure distillation to remove the organic acid solution until no liquid is in the microwave reaction chamber;
5) 5 L absolute ethanol is added into the microwave reaction chamber in step 4), sufficiently stirred, and filtered, wherein the filtrate is distilled to recover ethanol, and the residue after being dried is microwave pretreated *wakame* powder;
6) 100 g microwave pretreated *wakame* powder in step 5) is placed in a 1 L beaker, 500 ml distill water is added thereinto, and the mixer is placed in a hot water bath at 70° C. for 40 mins for extraction and then filtered. The above procedure is repeated once. The two filtrates are combined and pH thereof is adjusted to neutral, and residue is maintained for further process;
7), 8) steps are the same as ones in Example 1.

Data including extraction yields of products in each step, total water consumption in the process, viscosity of sodium alginate products, sulfate content of fucoidan, etc. are listed in Table 4.

TABLE 4

Comparison results of polysaccharide extraction yield of each step, the total amount of water consumption, the viscosity of sodium alginate and the sulfate content of fucoidan between using microwave pretreated wakame dry powder and using untreated wakame dry powder raw materials:

| | Comparative process | Novel Process |
|---|---|---|
| Water consumption (water/wakame powder) | 100/1 | 15/1 |
| Yield of sodium alginate (wt) | 15.8% | 11.0% (M Rich) 7.2% (G Rich) |
| Yield of algin (wt) | 2.1% | 5.2% |
| Yield of laminaran (wt) | 0.5% | 0.7% |
| Molecular weight of sodium alginate | $8.6 \times 10^5$ | $4.2 \times 10^4$ (M Rich) |
| Sulfate content of fucoidan (wt) | 19.0% | 7.2% |
| Amount of base (base/wakame powder) | 0.25 | 0.05 |
| Amount of organic acid solution (liquid/solid) | — | 2/3 |
| Sodium alginate M/G | 1.43 | 7.30 (M Rich) |
| Processing time (min) | 60 | 35 |

Comparative Example 5

Control process: 100 g *fucus* powder raw material after being washed, dried, pulverized is weighted and placed in a 2 L beaker, and 1 L water and 25 g sodium carbonate are added into the beaker. The mixer is stirred in a water bath of 70° C. for 1 hour, and then is diluted with 80-100 L water, followed by sufficient stirring and filtration. The filtrate is adjusted to pH 2.0 by adding hydrochloric acid and is centrifuged. The precipitate is converted to sodium alginate by adding sodium carbonate. The resulting supernatant is subjected to grading ethanol precipitation to obtain fucoidan (by adding ethanol up to the alcohol content of 65 wt %) and laminaran (by adding ethanol up to the alcohol content of 85 wt %). Parameters regarding the products are measured according to Comparative Example 1. All analysis results are shown in Table 5.

Example 5

The differences from Example 1 are:
1) 1.5 kg dry *fucus* powder after being dried, decontaminated and pulverized is placed in a resonant wave microwave reaction chamber;
2) 1.8 L anhydrous propanoic acid and 0.2 L water are mixed to prepare 2 L 90% propanoic acid solution;
3) 2 L propanoic acid solution in step 2) is added into the microwave reaction chamber in step 1), and the mixer is sufficiently stirred to evenly wet the *fucus* powder;
4) the wetted material in step 3) is subjected to irradiation at 4 KW continuous microwave power until liquid refluxes, i.e., the organic acid solution is vaporized, and then the microwave power is switched to 2 KW; after 30 mins, vacuuming is conducted (reaction chamber working pressure is 150 mmHg) for reduced pressure distillation for reduced pressure distillation to remove the organic acid until no liquid is in the microwave reaction chamber;
5) 5 L absolute ethanol is added into the microwave reaction chamber in step 4), sufficiently stirred, and filtered, wherein the filtrate is distilled to recover ethanol, and the residue after being dried is microwave pretreated *fucus* powder;
6) 100 g microwave pretreated *fucus* powder in step 5) is placed in a 1 L beaker, 500 ml distill water is added thereinto, and the mixer is placed in a hot water bath at 70° C. for 40 mins for extraction and then filtered. The above procedure is repeated once. The two filtrates are combined and pH thereof is adjusted to neutral, and residue is maintained for further process;
7), 8) steps are the same as ones in Example 1.

Data including extraction yields of products in each step, total water consumption in the process, viscosity of sodium alginate products, sulfate content of fucoidan, etc. are listed in Table 5.

TABLE 5

Comparison results of polysaccharide extraction yield of each step, the total amount of water consumption, the viscosity of sodium alginate and the sulfate content of fucoidan between using microwave pretreated fucus dry powder and using untreated fucus dry powder raw materials:

| | Comparative process | Novel Process |
|---|---|---|
| Water consumption (water/fucus powder) | 100/1 | 15/1 |

TABLE 5-continued

Comparison results of polysaccharide extraction yield of each step, the total amount of water consumption, the viscosity of sodium alginate and the sulfate content of fucoidan between using microwave pretreated *fucus* dry powder and using untreated *fucus* dry powder raw materials:

| | Comparative process | Novel Process |
|---|---|---|
| Yield of sodium alginate (wt) | 11.7% | 7.0% (M Rich) 6.2% (G Rich) |
| Yield of algin (wt) | 1.1% | 2.2% |
| Yield of laminaran (wt) | 0.6% | 0.7% |
| Molecular weight of sodium alginate | $6.7 \times 10^5$ | $2.2 \times 10^5$ (M Rich) |
| Sulfate content of fucoidan (wt) | 13.7% | 5.7% |
| Amount of base (base/*fucus* powder) | 0.25 | 0.05 |
| Amount of organic acid solution (liquid/solid) | — | 4/3 |
| Sodium alginate M/G | 2.53 | 5.90 (M Rich) |
| Processing time (min) | 60 | 30 |

Comparative Example 6

Control process: 100 g carrageen powder raw material after being washed, dried, pulverized is weighted and placed in a 2 L beaker, and 1 L water and 25 g sodium carbonate are added into the beaker. The mixer is stirred in a water bath of 70° C. for 1 hour, and then is diluted with 80-100 L water, followed by sufficient stirring and filtration. The filtrate is adjusted to pH 2.0 by adding hydrochloric acid and is centrifuged. The precipitate is converted to sodium alginate by adding sodium carbonate. The resulting supernatant is subjected to grading ethanol precipitation to obtain fucoidan (by adding ethanol up to the alcohol content of 65 wt %) and laminaran (by adding ethanol up to the alcohol content of 85 wt %). Parameters regarding the products are measured according to Comparative Example 1. All analysis results are shown in Table 6.

Example 6

The differences from Example 1 are:
1) 1.5 kg dry carrageen powder after being dried, decontaminated and pulverized is placed in a resonant wave microwave reaction chamber;
2) 300 g anhydrous oxalic acid and 1.5 L 0.12% hydrochloric acid solution are mixed to prepare about 1.5 L oxalic acid-hydrochloric acid mixed solution, wherein the content of oxalic acid is 20% and the content of hydrochloric acid is 0.1%;
3) 1.5 L oxalic acid-hydrochloric acid mixed solution in step 2) is added into the microwave reaction chamber in step 1), and the mixer is sufficiently stirred to evenly wet the carrageen powder;
4) the wetted material in step 3) is subjected to irradiation at 3 KW continuous microwave power until the liquid refluxes, i.e., the organic acid solution is vaporized, and then the microwave power is switched to 1.5 KW; after 30 mins, vacuuming is conducted (reaction chamber working pressure is 100 mmHg) for reduced pressure distillation until there is no liquid in the microwave reaction chamber;
5) 5 L absolute ethanol is added into the microwave reaction chamber in step 4), sufficiently stirred, and filtered, wherein the filtrate is distilled to recover ethanol and oxalic acid, and the residue after being dried is microwave pretreated carrageen powder;
6) 100 g microwave pretreated carrageen powder in step 5) is placed in a 1 L beaker, 500 ml distill water is added thereinto, and the mixer is placed in a hot water bath at 70° C. for 40 mins for extraction and then filtered. The above procedure is repeated once. The two filtrates are combined and pH thereof is adjusted to neutral, and residue is maintained for further process;
7), 8) steps are the same as ones in Example 1.

Data including extraction yields of products in each step, total water consumption in the process, viscosity of sodium alginate products, sulfate content of fucoidan, etc. are listed in Table 6.

TABLE 6

Comparison results of polysaccharide extraction yield of each step, the total amount of water consumption, the viscosity of sodium alginate and the sulfate content of fucoidan between using microwave pretreated carrageen dry powder and using untreated carrageen dry powder raw materials:

| | Comparative process | Novel Process |
|---|---|---|
| Water consumption (water/carrageen powder) | 100/1 | 15/1 |
| Yield of sodium alginate (wt) | 12.8% | 5.9% (M Rich) 7.4% (G Rich) |
| Yield of algin (wt) | 1.9% | 3.2% |
| Yield of laminaran (wt) | 0.8% | 0.8% |
| Molecular weight of sodium alginate | $7.7 \times 10^5$ | $1.6 \times 10^5$ (M Rich) |
| Sulfate content of fucoidan (wt) | 15.7% | 7.7% |
| Amount of base (base/carrageen powder) | 0.25 | 0.05 |
| Amount of organic acid solution (liquid/solid) | — | 1/1 |
| Sodium alginate M/G | 3.13 | 6.10 (M Rich) |
| Processing time (min) | 60 | 30 |

The examples's results show that the present invention uses microwave chemistry method to pretreat brown algae raw materials and then respectively uses water extraction and alkaline digestion to obtain uronic acid oligosaccharides and fucoidan oligosaccharides with different structures and to makes the sulfate content in fucoidan stay at a moderate range, while overcoming heavy water consumption, heavy pollution and many other shortcomings in the existing processes.

Experiment 1

Effects of *Japonica* Brown Algae Polysaccharides on Blood Glucose of Diabetic Mice Experiment animal: Kunming mice, male, weight (22±2) g, provided by the Experimental Animal Center of Military Medical Sciences, Beijing Experiment materials: streptozotocin (STZ) by Sigma, and *japonica* brown algae polysaccharides prepared in Example 1.

Main instruments and equipment: TU-1810 UV-Vis spectrophotometer, Beijing Purkinje General Instrument Co., Ltd.; BS-124S electronic balance, Sartorius AG, Germany; TGL-16G-A centrifuge, Shanghai Anting Scientific Instrument Factory; HPX-9052 MBE electric oven, Shanghai Haibo Motion Industries Limited; F6/10 superfine homogenizer, Shanghai Fluko Fluid Machinery Manufacturing Co., Ltd.

Experiment method: the mice are intraperitoneally injected with streptozotocin (STZ) 50 mg/kg, and ones with blood glucose ≥11.1 mmol/L are taken as a model for diabetes. 20 model mice, according to blood glucose level, are randomly assigned into model group and brown algae polysaccharides group. Another 10 normal mice are taken as a control group. Mice of each group are treated via gavage daily at 9:00 am wherein brown algae polysaccharides group is given a dose of 500 mg/kg, the model group and the control group are given corresponding volume of distilled water. The treatment is continued for 32 days, and mice are fasted but were feed with water for 12 h on the 21st day and the 32nd day. Blood samples are taken from orbital cavity, and serum is separated to detect fasting glucose values of the mice.

Statistical Method: statistical method uses SPSS statistical software, the data are all represented in ±s, and a comparative analysis between groups is analyzed by variance. The results are shown in the table below:

| Group | | Day 0 | Day 21 | Day 32 |
|---|---|---|---|---|
| Control Group | 10 | 4.88 ± 1.02 | 4.85 ± 1.13 | 4.79 ± 1.24 |
| Model Group | 10 | 13.22 ± 2.32 | 13.01 ± 4.34 | 12.58 ± 2.13 |
| Brown algae polysaccharides Group | 10 | 13.51 ± 3.24 | 10.21 ± 4.08 | 8.49 ± 3.22 |

Brown algae polysaccharides of the present invention can effectively and significantly reduce blood glucose in diabetic mice.

The invention claimed is:

1. A process of extracting brown algae active polysaccharides via a microwave chemistry method, wherein the process comprises the following steps:
   a) putting pulverized brown algae raw materials into a microwave reactor chamber, adding an acid solution of a mass concentration of 5% to 99% to the chamber, subjecting a mixture of the pulverized brown algae raw materials and the acid solution for 5 to 120 minutes to a microwave power of mass power density of 1 kilowatt per kilogram of material to 10 kilowatts per kilogram of material under a work pressure of 20 mmHg to 760 mmHg, and then washing the mixture with an organic solvent to remove excess acid;
   b) adding an aqueous solution into the product obtained from step a) for extraction, concentrating the extracting solution, adjusting pH to neutral by a base, conducting graded alcohol precipitation to respectively obtain mannuronic acid-rich fragment algin, fucoidan, and laminaran; and remaining brown algae residue; and
   c) adding an alkali solution to the brown algae residue of step b), conducting alkaline digestion reaction at a temperature of 35 to 60° C. for 20 to 80 minutes, filtering the residue off, adjusting pH of the filtrate to neutral, conducting alcohol precipitation to obtain guluronic acid rich fragment (G rich) algin precipitates.

2. The process of claim 1, wherein, the application mode of the microwave power in said step a) is a continuous microwave mode or a combination of continuous microwave and pulse microwave modes; wherein in case of using the combination of continuous microwave and pulse microwave, the continuous microwave irradiation is first used until a reflux of the acid solution, then is switched to pulse microwave irradiation for 5 to 120 minutes.

3. The process of claim 1, further comprising concentrating the mixture before washing the mixture with the organic solvent in step a), wherein the acid solution is volatile acid, and wherein the acid is removed during concentrating the mixture.

4. The process of claim 2, wherein, in said step a), in the case of continuous microwave, mass power density is 1 kilowatt per kilogram of material to 5 kilowatts per kilogram of material; in the case of pulse microwave, mass power density is 2 kilowatts per kilogram of material to 10 kilowatts per kilogram of material, the duty ratio is A/B, wherein A is on-time and B is off-time, and A=1 sec to 100 sec, B=1 sec to 100 sec.

5. The process of claim 1, wherein, in said step a), range of weight ratio of the brown algae raw material and the acid solution=5/1 to 1/5.

6. The process of claim 5, wherein, the acid solution used in step a) is selected from an organic acid or a mixed solution of an organic acid and an inorganic acid.

7. The process of claim 6, wherein, the organic acid in step a) is selected from oxalic acid of 5% to 50%; formic acid of 10% to 99%; acetic acid of 10% to 99%; or propionic acid of 10% to 99%.

8. The process of claim 6, wherein, in the mixed solution of organic acid and inorganic acid in said step a), the mass percentage concentration of the inorganic acid is 0.1% to 15%.

9. The process of claim 8, wherein, the inorganic acid in said step a) is selected from hydrochloric acid, sulfuric acid, nitric acid or phosphoric acid.

10. The process of claim 1, wherein, the organic solvent used to wash the residue acid in said step a) is selected from methanol, ethanol, propanol or acetone, or a combination of two or more thereof.

11. The process of claim 1, wherein, in the step b), the amount of water is 5 to 8 times of the volume of the product obtained in the step a).

12. The process of claim 1, wherein, in the step b), the base used for pH adjustment is selected from sodium carbonate or sodium hydroxide.

13. The process of claim 1, wherein, the graded alcohol precipitation in said step b) comprises: adding ethanol to 20 wt % to 40 wt % alcohol content, conducting centrifugation or filtration to obtain a mannuronic acid-rich fragment oligo algin precipitates; then adding ethanol to 60 wt % to 70 wt % alcohol content, conducting filtration or centrifugation to obtain fucoidan precipitates; and finally adding ethanol to 80 wt % to 85 wt % alcohol content, conducting filtration or centrifugation to obtain laminaran precipitates.

14. The process of claim 1, wherein, the base in said step c) is selected from sodium carbonate or sodium hydroxide.

15. The process of claim 1, wherein, an acid is used to adjust pH value in the step c) and selected from hydrochloric acid.

16. The process of claim 1, wherein, the alcohol in said step c) is selected from methanol or ethanol.

17. The process of claim 1, wherein, the brown algae is selected from *Laminaria japonica, Sargassum sargassum*, sea millet, *fusiforme, Sargassum*, creeping Sargasso sticks, *Fucus fucus*, bladderwrack, *Pelvetia carrageenan, Undaria wakame* and *Maerocystis kelp*.

18. The process of claim 17, wherein, the process of preparing active polysaccharides using *Laminaria japonica* comprises:
   putting dry *japonica* powder into a microwave extract chamber, adding 60% to 85% formic acid of 0.5 to 1.5 times of its weight to the chamber, at a microwave power density 1 to 2 KW/Kg under 500 mmHg to 760 mmHg pressure, maintaining a reflux of formic acid solution for 15 to 30 minutes, and then evaporating under reduced pressure the formic acid solution to dryness;

adding an ethanol solution of 3 to 5 times of the weight of the *japonica* powder to the reaction chamber;

stirring a mixture of the ethanol solution and the *japonica* powder for 40 to 60 minutes and filtering the mixture to obtain a filter residue filtered;

drying the filter residue and extracting the filter residue twice with water to obtain an extract, wherein each time the amount of water is 4 to 6 times of the weight of the residue, the extraction temperature is 60 to 80° C., and the extraction time is about 40 minutes;

neutralizing the extract with a sodium hydroxide solution, and concentrating the extract to a volume of 1/5 of the extract;

adding ethanol to the extract to have 35% ethanol content, and standing the extract for 4 to 8 hours and filtering the extract to obtain a first filtrate cake and a first filtrate;

washing the first filtrate cake with anhydrous ethanol and ether and drying the first filtrate cake to obtain polysaccharide A;

adding ethanol to the first filtrate to have 65% ethanol content, standing the first filtrate for 4 to 8 hours, and filtering the first filtrate to obtain a second filtrate cake and a second filtrate;

washing the second filtrate cake with anhydrous ethanol and ether and drying the second filtrate cake to obtain polysaccharide B;

adding ethanol to the second filtrate to have 85% ethanol content of the solution, standing the second filtrate for 4 to 8 hours, and filtering the second filtrate to obtain a third filtrate cake;

washing the third filtrate cake with anhydrous ethanol and ether and drying the third filtrate cake to obtain polysaccharide C;

adding a sodium carbonate solution to the residue after the step of extracting the filter residue twice with water, at a temperature of 35 to 60° C. for alkaline digestion reaction for about 40 minutes, filtering a mixture of the residue and the sodium carbonate solution to obtain a third filtrate, and neutralizing the third filtrate with hydrochloric acid, concentrating the third filtrate, and subjecting the third filtrate to alcohol precipitation to obtain polysaccharide D;

wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

19. The process of claim 17, wherein, the process of preparing active polysaccharides using *Sargassum fusiforme* comprises:

putting dry *fusiforme* powder into a microwave extract chamber, adding 10% to 20% oxalic acid solution of 0.5 to 1.5 times thereof to the chamber, at a microwave power density 1 to 2 KW/Kg under 500 mmHg to 760 mmHg pressure, maintaining a reflux of oxalic acid solution for 15 to 25 minutes, and then evaporating under reduced pressure the solution to dryness;

adding an ethanol solution of 4 to 6 times of the weight of the *fusiforme* powder to the reaction chamber;

stirring a mixture in the chamber for 40 to 60 minutes and filtering the mixture to obtain a filter residue and a filtrate;

drying the filter residue, and distilling the filtrate to recycle ethanol and oxalic acid;

extracting the filter residue twice with water to obtain an extract, wherein each time the amount of water is 4 to 6 times of the weight of the residue, the extraction temperature is 70° C., and the extraction time is about 40 minutes;

neutralizing the extract with a sodium hydroxide solution, and concentrating the extract to a volume of 1/5 of the extract;

adding ethanol to the extract to have 30% ethanol content, standing the extract for 4 to 8 hours, and filtering the extract to obtain a first filtrate cake and a first filtrate;

washing the first filtrate cake with anhydrous ethanol and ether and drying the first filtrate cake to obtain polysaccharide A;

adding ethanol to the first filtrate to have 60% ethanol content of the solution, standing the first filtrate for 4 to 8 hours, and filtering the first filtrate to obtain a second filtrate cake and a second filtrate;

washing the second filtrate cake with anhydrous ethanol and ether and drying the second filtrate cake to obtain polysaccharide B;

adding ethanol to the second filtrate to have 80% ethanol content of the solution, standing the second filtrate for 4 to 8 hours, and filtering the second filtrate to obtain a third filtrate cake;

washing the third filtrate cake with anhydrous ethanol and ether and drying the third filtrate cake to obtain polysaccharide C; and adding a sodium carbonate solution to the residue after the step of extracting the filter residue twice with water, at a temperature of 35 to 60° C. for alkaline digestion reaction for 40 to 60 minutes, filtering a mixture of the residue and the sodium carbonate solution to obtain a third filtrate, and neutralizing the third filtrate with hydrochloric acid, concentrating the third filtrate, and subjecting the third filtrate to alcohol precipitation to obtain polysaccharide D;

wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

20. The process of claim 17, wherein, the process of preparing active polysaccharides using *Fucus fucus* comprises:

putting dry *fucus* powder into a microwave extract chamber, adding 80% to 95% propionic acid solution of 1 to 2 times thereof to the chamber, at a microwave power density 3 to 5 KW/Kg, after propionic acid solution refluxes, maintaining for 40 to 60 minutes under 500 mmHg to 760 mmHg pressure, and then evaporating under reduced pressure the propionic acid solution to dryness;

adding an ethanol solution of 3 to 5 times of the weight of the *fucus* powder to the reaction chamber;

stirring a mixture in the chamber for 30 to 60 minutes and filtering the mixture to obtain a filter residue;

drying the filter residue;

extracting the filter residue twice with water of 4 to 6 times of the weight of the residue at 70° C. for 40 minutes and filtering a mixture of the filter residue and the water to obtain an extract;

neutralizing the extract with a sodium hydroxide solution, and concentrating the extract to a volume of 1/5 of the extract;

adding ethanol to the extract to have 35% ethanol content, standing the extract for 4 to 8 hours, and filtering the extract to obtain a first filtrate cake and a first filtrate;

washing the first filtrate cake with anhydrous ethanol and ether and drying the first filtrate cake to obtain polysaccharide A;

adding ethanol to the first filtrate to have 65% ethanol content, standing the first filtrate for 4 to 8 hours, and filtering the first filtrate to obtain a second filtrate cake and a second filtrate;

washing the second filtrate cake with anhydrous ethanol and ether and drying the second filtrate cake to obtain polysaccharide B;

adding ethanol to the second filtrate to have 85% ethanol content, standing the second filtrate for 4 to 8 hours, and filtering the second filtrate to obtain a third filtrate cake;

washing the third filtrate cake with anhydrous ethanol and ether and drying the third filtrate cake to obtain polysaccharide C; and adding a sodium carbonate solution to the residue after the step of extracting the filter residue twice with water, at a temperature of 35 to 60° C. for alkaline digestion reaction for 40 to 60 minutes, filtering a mixture of the residue and the sodium carbonate solution to obtain a third filtrate, and neutralizing the third filtrate with hydrochloric acid, concentrating the third filtrate, and subjecting the third filtrate to alcohol precipitation to obtain polysaccharide D;

wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

21. The process of claim 17, wherein, the process of preparing active polysaccharides using *Pelvetia carrageenan* comprises:

putting dry *carrageenan* powder into a microwave extract chamber, adding an oxalic acid-hydrochloric acid mixed solution of 0.5 to 2 times thereof to the chamber wherein the content of oxalic acid in the mixed solution is 20% and the content of hydrochloric acid is 0.1%, at a microwave power density 1 to 2 KW/Kg under 500 mmHg to 760 mmHg pressure maintaining a reflux of mixed acid solution for 15 to 25 minutes, and then evaporating under reduced pressure the solution to dryness;

adding an ethanol solution of 3 to 5 times of the weight of the *carrageenan* powder to the reaction chamber;

stirring a mixture in the chamber for 30 to 60 minutes and filtering the mixture to obtain a filter residue;

drying the filter residue;

extracting the filter residue twice with water of 4 to 6 times of the weight of the residue, at 70° C. for 40 minutes, and filtering a mixture of the filter residue and the water to obtain an extract;

neutralizing the extract with a sodium hydroxide solution, concentrating the extract to a volume of 1/5 of the extract;

adding ethanol to the extract to have 35% ethanol content, standing the extract for 4 to 8 hours, and filtering the extract to obtain a first filtrate cake and a first filtrate;

washing the first filtrate cake with anhydrous ethanol and ether and drying the first filtrate cake to obtain polysaccharide A;

adding ethanol to the first filtrate to have 65% ethanol content, standing the first filtrate for 4 to 8 hours, and filtering the first filtrate to obtain a second filtrate cake and a second filtrate;

washing the second filtrate cake with anhydrous ethanol and ether and drying the second filtrate cake to obtain polysaccharide B;

adding ethanol to the second filtrate to have 85% ethanol content, standing the second filtrate for 4 to 8 hours, and filtering the second filtrate to obtain a third filtrate cake;

washing the third filtrate cake with anhydrous ethanol and ether and drying the third filtrate to obtain polysaccharide C; and adding a sodium carbonate solution to the residue after the step of extracting the filter residue twice with water, at a temperature of 35 to 60° C. for alkaline digestion reaction for 40 to 60 minutes, filtering a mixture of the residue and the sodium carbonate solution to obtain a third filtrate, and neutralizing the third filtrate with hydrochloric acid, concentrating the third filtrate, and subjecting the third filtrate to alcohol precipitation to obtain polysaccharide D;

wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

22. The process of claim 17, wherein, the process of preparing active polysaccharides using *Undaria wakame* comprises:

putting dry *wakame* powder into a microwave extract chamber, adding formic acid-hydrochloric acid mixed solution of 0.5 to 2.5 times thereof to the chamber, wherein the content of formic acid is 80% and the content of hydrochloric acid is 0.5%, at a microwave power density 2 to 4 KW/Kg under 500 mmHg to 760 mmHg pressure, maintaining a reflux of mixed acid solution for 10 to 30 minutes, and then evaporating under reduced pressure the mixed acid solution to dryness;

adding an ethanol solution of 3 to 5 times of the weight of the *wakame* powder to the reaction chamber;

stirring a mixture in the chamber for 30 to 60 minutes and filtering the mixture to obtain a filter residue;

drying the filter residue;

extracting the filter residue twice with water of 4 to 6 times of the weight of the residue, at 60° C. for 40 minutes, and filtering a mixture of the filter residue and the water to obtain an extract;

neutralizing the extract with a sodium hydroxide solution, and concentrating the extract to a volume of 1/5 of the extract;

adding ethanol to the extract to have 35% ethanol content, standing the extract for 4 to 8 hours, and filtering the extract to obtain a first filtrate cake and a first filtrate;

washing the first filtrate cake with anhydrous ethanol and ether and drying the first filtrate cake to obtain polysaccharide A;

adding ethanol to the first filtrate to have 65% ethanol content, standing the first filtrate for 4 to 8 hours, and filtering the first filtrate to obtain a second filtrate cake and a second filtrate;

washing the second filtrate cake with anhydrous ethanol and ether and drying the second filtrate cake to obtain polysaccharide B;

adding ethanol to the second filtrate to have 85% ethanol content, standing the second filtrate for 4 to 8 hours, and filtering the second filtrate to obtain a third filtrate cake;

washing the third filtrate cake with anhydrous ethanol and ether and drying the third filtrate cake to obtain polysaccharide C; and adding a sodium carbonate solution to the residue after the step of extracting the filter residue twice with water, at a temperature of 35 to 60° C. for alkaline digestion reaction for 40 to 60 minutes, filtering a mixture of the residue and the sodium carbonate solution to obtain a third filtrate, and neutralizing the third filtrate with hydrochloric acid, concentrating the third filtrate, and subjecting the third filtrate to alcohol precipitation to obtain polysaccharide D;

wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

23. The process of claim 17, wherein, the process of preparing active polysaccharides using *Maerocystis kelp* comprises:

putting dry *kelp* powder into a microwave extract chamber, adding 80% to 95% acetic acid solution of 0.3 to 1.2 times thereof to the chamber, at a microwave power density 1 to 4 KW/Kg under 500 mmHg to 760 mmHg pressure maintaining a reflux of acetic acid solution for 30 to 40 minutes, and then evaporating under reduced pressure the formic acid solution to dryness;

adding an ethanol solution of 3 to 5 times of the weight of the *kelp* powder to the reaction chamber;

stirring a mixture in the chamber for 30 to 60 minutes and filtering the mixture to obtain a filter residue;

drying the filter residue;

extracting the filter residue twice with water of 4 to 6 times of the weight of the residue, at 60° C. for 40 minutes, and filtering a mixture of the filter residue and the water to obtain an extract;

neutralizing the extract with a sodium hydroxide solution, concentrating the extract to a volume of 1/5 of the extract;

adding ethanol to the extract to have 35% ethanol content, standing the extract for 4 to 8 hours, and filtering the extract to obtain a first filtrate cake and a first filtrate;

washing the first filtrate cake with anhydrous ethanol and ether and drying the first filtrate cake to obtain polysaccharide A;

adding ethanol to the first filtrate to have 65% ethanol content, standing the first filtrate for 4 to 8 hours, and filtering the first filtrate to obtain a second filtrate cake and a second filtrate;

washing the second filtrate cake with anhydrous ethanol and ether and drying the second filtrate to obtain polysaccharide B;

adding ethanol to the second filtrate to have 85% ethanol content, standing the second filtrate for 4 to 8 hours, and filtering the second filtrate to obtain a third filtrate cake;

washing the third filtrate cake with anhydrous ethanol and ether and drying the third filtrate cake to obtain polysaccharide C; and adding a sodium carbonate solution to the residue after the step of extracting the filter residue twice with water, at a temperature of 35 to 60° C. for alkaline digestion reaction for 40 to 60 minutes, filtering a mixture of the residue and the sodium carbonate solution to obtain a third filtrate, and neutralizing the third filtrate with hydrochloric acid, concentrating the third filtrate, and subjecting the third filtrate to alcohol precipitation to obtain polysaccharide D;

wherein, polysaccharide A is mannuronic acid-rich (M rich) sodium alginate, polysaccharide B is fucoidan, polysaccharide C is laminaran, and polysaccharide D is guluronic acid-rich (G rich) sodium alginate.

24. The process of claim 1, wherein, the prepared brown algae polysaccharides is a guluronic acid-rich fragment algin or a mannuronic acid-rich fragment algin.

25. The process of claim 24, wherein, the prepared guluronic acid-rich fragment algin is guluronic acid-rich fragment *japonica* algin, *fusiforme* algin, *fucus* algin, carrageen algin, *wakame* algin, or *kelp* align.

26. The process of claim 24, wherein, the prepared mannuronic acid-rich fragment algin is mannuronic acid-rich fragment *japonica* algin, *fusiforme* algin, *fucus* algin, carrageen algin, *wakame* algin, or *kelp* align.

27. A process of preparing mannuronic acid-rich fragment sodium alginate, wherein, the mannuronic acid-rich fragment algin prepared using the process of claim 1 is added with sodium carbonate to be converted to the mannuronic acid-rich fragment sodium alginate.

* * * * *